United States Patent [19]

Maignan et al.

[11] Patent Number: 4,512,985
[45] Date of Patent: Apr. 23, 1985

[54] N-CARBAMOYL DERIVATIVES OF (5,4B)-ISOTHIAZOLO PYRIDINE-3-ONE AND ANTI-ACNE COSMETIC COMPOSITIONS CONTAINING THE SAME

[75] Inventors: Jean Maignan, Tremblay-les-Gonesse; Braham Shroot, Antibes, both of France

[73] Assignee: Societe Anonyme dite: L'Oreal, Paris, France

[21] Appl. No.: 484,619

[22] Filed: Apr. 13, 1983

[30] Foreign Application Priority Data

Apr. 16, 1982 [LU] Luxembourg ............................ 84091

[51] Int. Cl.³ ............................................ A61K 31/425
[52] U.S. Cl. ..................................... 514/301; 546/114; 514/859
[58] Field of Search ................. 546/114; 424/256, 232

[56] References Cited

U.S. PATENT DOCUMENTS 3,965,107 6/1976 Rainey et al. ........................ 546/114

OTHER PUBLICATIONS

Fischer et al., "Arzneimittel-Forsch", vol. 14(12), pp. 1301–1306, (1964).
McClelland et al., J. Chem. Soc., pp. 921–926, (1926).

Primary Examiner—Henry R. Jiles
Assistant Examiner—Bernard I. Dentz
Attorney, Agent, or Firm—Cushman, Darby & Cushman

[57] ABSTRACT

N-carbamoyl derivatives of (5,4b)-isothiazolo pyridine-3-one have the formula

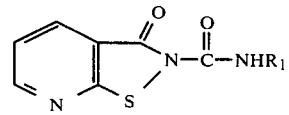

wherein $R_1$ represents hydrogen, linear or branched alkyl having 1–12 carbon atoms, cycloalkyl having 3–6 carbon atoms or

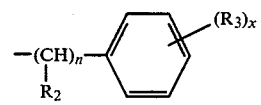

wherein n is 0 or 1, x is 1, 2 or 3, $R_2$ represents hydrogen or lower alkyl having 1–3 carbon atoms and $R_3$ represents hydrogen, lower alkyl having 1–3 carbon atoms, nitro, trifluoromethyl or halogen. These derivatives are useful in the treatment of acne.

9 Claims, No Drawings

N-CARBAMOYL DERIVATIVES OF (5,4B)-ISOTHIAZOLO PYRIDINE-3-ONE AND ANTI-ACNE COSMETIC COMPOSITIONS CONTAINING THE SAME

The present invention relates to new N-carbamoyl derivatives of (5,4b)isothiazolo pyridine-3-one, which are particularly useful in the treatment of acne. Moreover, the present invention relates to a process for preparing these derivatives and to anti-acne cosmetic compositions containing them.

The present invention more particularly relates to, as a new industrial product, N-carbamoyl derivatives of (5,4b)isothiazolo-pyridine-3-one having the formula

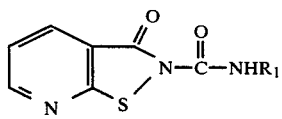

wherein $R_1$ represents hydrogen, linear or branched alkyl having 1-12 carbon atoms, cycloalkyl having 3-6 carbon atoms or

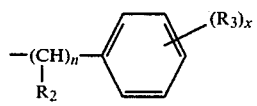

wherein n is 0 or 1, x is 1, 2 or 3, $R_2$ represents hydrogen or lower alkyl having 1-3 carbon atoms and $R_3$ represents hydrogen, lower alkyl having 1-3 carbon atoms, nitro, trifluoromethyl or a halogen such as Br, Cl or F, and to their salts of a mineral or organic acid, as well as to their optical isomers when $R_2$ represents alkyl and n is 1.

When $R_1$ is linear or branched alkyl having 1-12 carbon atoms, it is preferably methyl, ethyl, propyl, isopropyl, butyl, heptyl or nonyl.

When $R_1$ is cycloalkyl, it is, preferably, cyclopentyl or cyclohexyl.

When $R_1$ has the value represented by formula II, it is, preferably, phenyl, benzyl, p-tolyl, 2′,5′-dichlorophenyl, 2′,4′-dichlorophenyl, 4′-chlorophenyl, 4′-nitrophenyl, 4′-methylbenzyl, 4′-nitrobenzyl, 4′-chlorobenzyl, 2′,4′-dichlorobenzyl and 2′,5′-dichlorobenzyl.

Representative compounds of Formula I include particularly the following:

(1) 2-(N-methyl carbamoyl)-(5,4b)isothiazolo pyridine-3-one,
(2) 2-(N-butyl carbamoyl)-(5,4b)isothiazolo pyridine-3-one,
(3) 2-(N-isopropyl carbamoyl)-(5,4b)isothiazolo pyridine-3-one,
(4) 2-(N-heptyl carbamoyl)-(5,4b)isothiazolo pyridine-3-one,
(5) 2-(N-nonyl carbamoyl)-(5,4b)isothiazolo pyridine-3-one,
(6) 2-(N-cyclohexyl carbamoyl)-(5,4b)isothiazolo pyridine-3-one,
(7) 2-(N-phenyl carbamoyl)-(5,4b)isothiazolo pyridine-3-one, and their salts of a mineral or organic acid selected from the group consisting of hydrochloric acid, hydrobromic acid, acetic acid, citric acid, malic acid, tartaric acid, succinic acid, salicyclic acid and retinoic acid.

The compounds according to the present invention are obtained in accordance with the following reaction scheme:

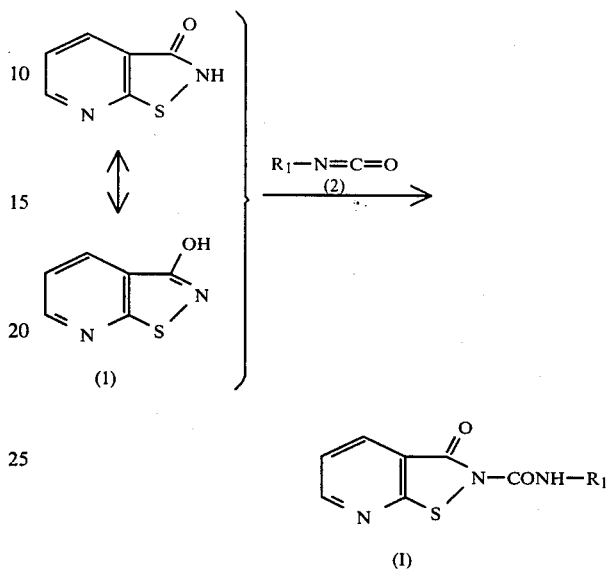

This process comprises reacting (5,4b)-isothiazolo pyridine-3-one, or 3-hydroxy-(5,4b)isothiazolo pyridine, (1) with an isocyanate (2) in an anhydrous organic solvent, preferably tetrahydrofuran (THF) at a temperature generally between −10° and +60° C. and preferably at ambient temperature.

The reaction can be carried out in the presence of a base such as 1,5-diaza-[5.4.0]bicyclo-5-undecene (DBU).

If the expected product does not crystallize in the solvent, the latter is then evaporated under reduced pressure and the residue is then recrystallized in an appropriate organic solvent, preferably a chlorinated or aromatic solvent, or purified by chromatography on silica gel.

The initial reactant, (5,4b)-isothiazolo pyridine-3-one (1) is a known compound.

The present invention also relates to an anti-acne cosmetic composition containing as the active component at least one compound of formula I, as defined above.

Acne is generally manifested by the appearance of pimples, blackheads or pustules on the face, the neck and at times on the back and chest. This manifestation of acne is caused, essentially, by hyperkertinization of the ducts of the sebaceous glands. As a result the sebum, which is not able to flow freely forms a favorable environment for bacterial proliferation. This leads to certain inflammation phenomena, the bacteria being in effect capable of rupturing the ducts of the sebaceous glands which free irritating fatty acids.

In an effort to avoid such irritation phenomena it is important to employ certain substances capable of acting, in an efficacious manner, with regard to the principal germs associated with acne, i.e. *Corinebacterium acnes* and *Propionibacterium granulosum*.

When the activity of these germs are inhibited the hydrolytic cleavage of normal triglycerides of the sebum is avoided thereby preventing the formation of long chain fatty acids, the presence of which, as has been noted, causes typical inflammation phenomena of acne lesions.

The new compounds according to the present invention are, in this respect, excellent anti-acne agents especially since they have been established as being particularly active with regard to the two principal germs associated with acne, i.e. *Corinebacterium acnes* and *Propionibacterium granulosum*.

In the compositions according to the invention the concentration of the compound of formula I is generally between 0.1 and 10 weight percent, but preferably between 0.5 and 3 weight percent, based on the total weight of the composition.

These compositions can be provided under various forms appropriate for topical application to the area of the skin to be treated and principally in the form of lotions, ointments, tinctures, creams, gels or as an aerosol preparation.

The lotions are aqueous or hydroalcoholic preparations which can also contain certain suspension or dispersion agents, such as derivatives of cellulose, gelatin and gums. Glycerine or propylene glycol can also be included in these lotions.

The tinctures are alcoholic or hydroalcoholic solutions formulated with an alcohol, such as ethanol or isopropanol.

The gels are semi-solid preparations prepared by gelification of a solution or suspension of a compound of formula I using a gelling agent such as "Bentone gel" (sold by NL Industries) for a fatty phase, or crosslinked polyacrylic acid, for an aqueous phase, this polyacrylic acid being sold by Goodrich under the tradename "Carbopol", and being employed in the neutralized form.

In accordance with a embodiment, the compositions according to the invention are provided in the form of a cream, that is, in the form of a water-in-oil or oil-in-water type emulsion.

In order to reinforce the anti-acne activity of the compounds of formula I, it is possible to use, in accordance with the invention, certain antibiotics such as the tetracyclines such as, chlortetracycline or oxytetracycline or macrolids, such as erythromycin, aminosides such as neomycin, sulfamides (sulfanilamides), synergistines, A.B. polypeptides or chloramphenicol.

The treatment of acne using the compositions according to the present invention comprises applying a sufficient amount of the composition, two or three times each day, on the area of the skin to be treated and this for a period of time ranging from one to four weeks.

The following non-limiting examples are given to illustrate the present invention.

EXAMPLE 1

2-(N-methyl carbamoyl-(5,4b)isothiazolo pyridine-3-one (Compound 1)

A mixture of 1.5 g of (5,4b)-isothiazolo pyridine-3-one (or 3-hydroxy-(5,4b)isothiazolo pyridine), 4 cm³ of methyl isocyanate and 2 drops of 1,5-diaza-[5.4.0]bicyclo-5-undecene (DBU) in 50 cm³ of anhydrous tetrahydrofuran is left to stand for 24 hours at ambient temperature.

The solid which precipitates in the mixture is then filtered, and subsequently crystallized in a chloroform-methanol mixture. The filtrate is concentrated and the residue recrystallized in this same chloroform-methanol mixture.

The 2-(N-methyl carbamoyl)-(5,4b)-isothiazolo pyridine-3-one, isolated in a yield of 45%, is provided in the form of very light yellow shiny flakes having a melting point of 209° C.

| Elemental analysis: $C_8H_7N_3O_2S$ | | | | |
|---|---|---|---|---|
| Calculated: | C 45.92 | H 3.37 | N 20.08 | S 15.32 |
| Theoretical: | 46.12 | 3.78 | 19.98 | 15.06 |

EXAMPLE 2

2-(N-butyl carbamoyl)-(5,4b)-isothiazolo pyridine-3-one (Compound 2)

A mixture of 1 g of (5,4b)-isothiazolo pyridine-3-one, 2 equivalents of N-butyl isocyanate and 2 drops of DBU in 40 cm³ of THF is stirred at ambient temperature for about 2 hours.

After the end of the reaction, the solvent is evaporated under reduced pressure and the resulting crystallized residue is dissolved in benzene.

The benzene phase is then submitted to chromatography on silica gel. After elution using chloroform and concentration of the elution solvent, recrystallization of the residue in a hexane-benzene mixture leads to a yield of about 53% of the expected product which is provided in the form of white crystals having a melting point of 116° C.

| Elemental analysis: $C_{11}H_{13}N_3O_2S$ | | | | |
|---|---|---|---|---|
| Calculated: | C 52.57 | H 5.21 | N 16.72 | S 12.76 |
| Theoretical: | 52.40 | 4.97 | 16.68 | 12.32 |

EXAMPLE 3

2-(N-isopropyl carbamoyl)-(5,4b)isothiazolo pyridine-3-one (Compound 3)

A mixture of 6 g of (5,4b)-isothiazolo pyridine-3-one, 3.2 cm³ of isopropyl isocyanate (10% excess) in 250 cm³ of anhydrous THF is left under agitation at ambient temperature and out of contact with the humidity of the air and light for a period of 48 hours.

The (5,4b)-isothiazolo pyridine-3-one progressively passes into solution during the course of this period, but the reaction is completed by adding 1 cm³ of isopropyl isocyanate. The reaction mixture is then left to stand for 24 hours, after which the solvent is evaporated under reduced pressure. The resulting white crystallized product is then washed twice with hexane and then dried with a dessicator, yielding 8 g of the expected product whose melting point is 164° C.

| Elemental analysis: $C_{10}H_{11}N_3O_2S$ | | | | |
|---|---|---|---|---|
| Calculated: | C 50.61 | H 4.67 | N 17.70 | S 13.51 |
| Theoretical: | 50.59 | 4.68 | 17.70 | 13.52 |

EXAMPLE 4

2-(N-heptyl carbamoyl)-(5,4b)isothiazolo pyridine-3-one (Compound 4)

Starting with 5 g of (5,4b)-isothiazolo pyridine-3-one and 5.5 g of heptyl isocyanate in 200 cm³ of THF, a white powder is obtained after 72 hours of agitation at ambient temperature and after removal of the solvent. The powder is then stirred in solution in dichloromethane in the presence of 5 g of silica gel which fixes any trace of the initial reactant, (5,4b)-isothiazolo pyridine-3-one, that remains unreacted. After filtration and concentration of the filtrate 7.5 g of white crystals having a melting point of 106° C. are obtained.

| Elemental analysis: $C_{14}H_{19}N_3O_2S$ | | | | |
| --- | --- | --- | --- | --- |
| Calculated: | C 57.31 | H 6.52 | N 14.32 | S 10.92 |
| Theoretical: | 57.44 | 6.53 | 14.29 | 10.76 |

EXAMPLE 5

2-(N-nonyl carbamoyl)-(5,4b)-isothiazolo pyridine-3-one (Compound 5)

This compound is obtained using nonyl isocyanate as an initial reactant and following essentially the procedures outlined above.

At the end of the reaction, the solvent is evaporated under reduced pressure. The resulting solid is washed twice with hexane and then dried, yielding 8 g of a white powder whose melting point is 102° C.

| Elemental analysis: $C_{16}H_{23}N_3O_2S$ | | | | |
| --- | --- | --- | --- | --- |
| Calculated: | C 59.78 | H 7.21 | N 13.07 | S 9.97 |
| Theoretical | 59.65 | 7.15 | 13.12 | 9.90 |

EXAMPLE 6

2-(N-cyclohexyl carbamoyl)-(5,4b)isothiazolo pyridine-3-one (Compound 6)

This compound is obtained using cyclohexyl isocyanate as an initial reactant and following essentially the procedures set forth above.

After evaporation of the solvent under reduced pressure 8.5 g of the expected product in the form of white crystals having a melting point of 146° C. are obtained.

| Elemental analysis: $C_{13}H_{15}N_3O_2S$ | | | | |
| --- | --- | --- | --- | --- |
| Calculated: | C 56.29 | H 5.45 | N 15.15 | S 11.56 |
| Theoretical: | 56.17 | 5.47 | 15.17 | 11.48 |

EXAMPLE 7

2-(N-phenyl carbamoyl)-(5,4b)-isothiazolo pyridine-3-one (Compound 7)

This compound is obtained using phenyl isocyanate as an initial reactant and following the above described procedures.

After evaporation of the solvent under reduced pressure and recrystallization of the resulting residue in dichloromethane 6.2 g of white crystals having a melting point of 174° C. are obtained.

| Elemental analysis: $C_{13}H_9N_3O_2S$ | | | | |
| --- | --- | --- | --- | --- |
| Calculated: | C 57.55 | H 3.34 | N 15.48 | S 11.81 |
| Theoretical: | 57.55 | 3.33 | 15.37 | 11.87 |

EXAMPLE 8

Preparation of 2-(N-phenyl carbamoyl)-(5,4b)-isothiazolo pyridine-3-one trans-retinoate To a solution of 1.2 g of trans-retinoic acid in 200 cm³ of anhydrous dichloromethane, placed in an inert atmosphere and out of contact with light, there are added 1.19 g of 2-(N-phenyl carbamoyl)-(5,4b)-isothiazolo pyridine-3-one.

The resulting mixture is magnetically stirred for one quarter hour, after which the solution is concentrated under reduced pressure until the salt begins to crystallize. There are then added 50 cm³ of pentane to crystallize all of the salt formed.

The resulting solid is filtered, washed with pentane and dried under reduced pressure.

2.1 g of yellow crystals having a melting point of 161° C. are obtained.

| Analysis: $C_{33}H_{37}N_3O_4S$ | | | | | |
| --- | --- | --- | --- | --- | --- |
| Calculated: | C 69.32 | H 6.52 | N 7.35 | O 11.19 | S 5.60 |
| Theoretical: | 69.32 | 6.63 | 7.30 | 11.34 | 5.55 |

EXAMPLE 9

Preparation of 2-(N-isopropyl carbamoyl)-(5,4b)-isothiazolo pyridine-3-one trans-retinoate Starting with 1.2 g of trans-retinoic acid and 0.96 g of 2-(N-isopropyl carbamoyl)-(5,4b)-isothiazolo pyridine-3-one and following the procedures of Example 8, 2 g of yellow crystals having a melting point of 155° C. are obtained.

| Analysis: $C_{30}H_{39}N_3O_4S$ | | | | | |
| --- | --- | --- | --- | --- | --- |
| Calculated: | C 67.01 | H 7.31 | N 7.81 | O 11.90 | S 5.96 |
| Theoretical | 67.07 | 7.30 | 7.69 | 11.84 | 5.97 |

EXAMPLE 10

Preparation of 2-(N-nonyl carbamoyl)-(5,4b)-isothiazolo pyridine-3-one trans-retinoate In accordance with the same procedures outlined in Example 8 and starting with 1.20 g of trans-retinoic acid and 1.28 g of 2-(N-nonyl carbamoyl)-(5,4b)-isothiazolo pyridine-3-one, 2.3 g of light yellow crystals of the sought after salt having a melting point of 135°–136° C. are obtained.

| Analysis: $C_{36}H_{51}N_3O_4S$ | | | | | |
| --- | --- | --- | --- | --- | --- |
| Calculated: | C 69.52 | H 8.26 | N 6.75 | O 10.29 | S 5.15 |
| Theoretical: | 69.58 | 8.32 | 6.91 | 10.16 | 5.01 |

EXAMPLE 11

Preparation of 2-(N-cyclohexyl carbamoyl)-(5,4b)-isothiazolo pyridine-3-one trans-retinoate Starting with 1.2 g of trans-retinoic acid and 1.11 g of 2-(N-cyclohexyl carbamoyl)-(5,4b)-isothiazolo pyridine-3-one and following essentially the procedures of Example 8, 2.1 g of the desired salt having a light yellow color are obtained.

| Analysis: $C_{33}H_{43}N_3O_4S$ | | | | | |
|---|---|---|---|---|---|
| Calculated: | C 68.60 | H 7.50 | N 7.27 | O 11.07 | S 5.54 |
| Theoretical: | 68.61 | 7.48 | 7.22 | 11.15 | 5.76 |

EXAMPLE 12

Preparation of 2-(N-nonyl carbamoyl)-(5,4b)-isothiazolo pyridine-3-one salicylate In accordance with the procedures set forth in Example 8, there is added to a solution of 0.56 g of salicyclic acid in 100 cm³ of methylene chloride one equivalent of 2-(N-nonyl carbamoyl)-(5,4b)-isothiazolo pyridine-3-one (1.21 g). After concentration of the reaction medium, the salt is precipitated by the addition of pentane. The salt is then filtered, washed with pentane and finally dried, yielding 1.65 g of white crystals having a melting point of 80° C.

| Analysis: $C_{23}H_{29}N_3O_5S$ | | | | | |
|---|---|---|---|---|---|
| Calculated: | C 60.11 | H 6.36 | N 9.14 | O 17.40 | S 6.97 |
| Theoretical: | 59.96 | 6.39 | 9.09 | 17.28 | 6.77 |

EXAMPLE 13

Preparation of 2-(N-cyclohexyl carbamoyl)-(5,4b)-isothiazolo pyridine-3-one salicylate Starting with 0.568 g of salicylic acid and 1.2 g of 2-(N-cyclohexyl carbamoyl)-(5,4b)-isothiazolo pyridine-3-one and following the procedures of Example 8, 1.7 g of a white powder having a melting point of 106° C. are obtained.

| Analysis: $C_{20}H_{21}N_3O_5S$ | | | | | |
|---|---|---|---|---|---|
| Calculated: | C 57.82 | H 5.09 | N 10.11 | O 19.25 | S 7.71 |
| Theoretical: | 57.74 | 5.04 | 10.03 | 19.45 | 7.55 |

EXAMPLES OF ANTI-ACNE COMPOSITIONS

EXAMPLE A

An anti-acne milk composition is prepared by admixing the following components:

| | |
|---|---|
| 2-(N—isopropyl carbamoyl)-(5,4b)-isothiazolo pyridine-3-one (Compound No. 3) | 0.5 g |
| Crosslinked polyacrylic acid, sold under the tradename "Carbopol 934" | 0.375 g |
| Isopropyl ester of fatty acids of lanolin | 1 g |
| Oxyethylenated lanolin | 2.5 g |
| Oxyethylenated cetylstearyl alcohol | 3 g |
| Substituted alkylamide | 20 cm³ |
| Methyl parahydroxybenzoate | 0.1 g |
| Propyl parahydroxybenzoate | 0.1 g |
| Water, sufficient amount for | 100 cm³ |

Additional comparably effective compositions are produced by replacing Compound No. 3 of this example with an equivalent amount of one of Compounds No. 5 or No. 6 or a salt of these compounds with salicylic acid (Examples Nos. 12 and 13), or with trans-retinoic acid (Examples Nos. 10 and 11).

EXAMPLE 13

An anti-acne cream is prepared by admixing the following components:

| | |
|---|---|
| 2-(N—phenyl carbamoyl)-(5,4b)-isothiazolo pyridine-3-one (Compound No. 7) | 0.5 g |
| Oxyethylenated cetylstearyl alcohol | 9 g |
| Silicone oil | 2 g |
| Diethyleneglycol stearate | 8 g |
| Methyl parahydroxybenzoate | 0.1 g |
| Propyl parahydroxybenzoate | 0.1 g |
| Water, sufficient amount for | 100 cm³ |

Additional comparably effective compositions are produced by replacing Compound No. 7 of this example with an equivalent amount of one of Compounds Nos. 1, 2 or 4, or a salt of Compound No. 7 with trans-retinoic acid (Example 8).

What is claimed is:

1. N-carbamoyl derivative of (5,4b)-isothiazolo pyridine-3-one having the formula

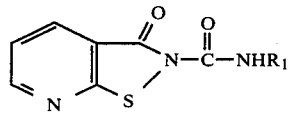

wherein
$R_1$ represents hydrogen, linear or branched alkyl having 1–12 carbon atoms, cycloalkyl having 3–6 carbon atoms or

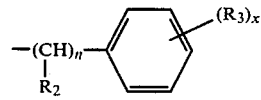

wherein n is 0 or 1, x is 1, 2 or 3, $R_2$ represents hydrogen or lower alkyl having 1–3 carbon atoms and $R_3$ represents hydrogen, lower alkyl having 1–3 carbon atoms, nitro, trifluoromethyl or halogen,
the salts thereof with a mineral or organic acid and the optical isomers thereof when $R_2$ represents alkyl and n equals 1.

2. The derivative of claim 1 wherein $R_1$ is a linear or branched alkyl selected from the group consisting of methyl, ethyl, propyl, isopropyl, butyl, heptyl and nonyl.

3. The derivative of claim 1 where $R_1$ is cycloalkyl selected from the group consisting of cyclopentyl and cyclohexyl.

4. The derivative of claim 1 wherein $R_1$ is

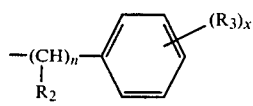

and is selected from the group consisting of phenyl, benzyl, p-tolyl, 2',5'-dichlorophenyl, 2',4'-dichlorophenyl, 4'-chlorophenyl, 4'-nitrophenyl, 4'-methylbenzyl, 4'-nitrobenzyl, 4'-chlorobenzyl, 2',4'-dichlorobenzyl and 2',5'-dichlorobenzyl.

5. The derivative of claim 1 selected from the group consisting of:
  (1) 2-(N-methyl carbamoyl)-(5,4b)isothiazolo pyridine-3-one,
  (2) 2-(N-butyl carbamoyl)-(5,4b)-isothiazolo pyridine-3-one,
  (3) 2-(N-isopropyl carbamoyl)-(5,4b)-isothiazolo pyridine-3-one,
  (4) 2-(N-heptyl carbamoyl)-(5,4b)-isothiazolo pyridine-3-one,
  (5) 2-(N-nonyl carbamoyl)-(5,4b)-isothiazolo pyridine-3-one,
  (6) 2-(N-cyclohexyl carbamoyl)-(5,4b)-isothiazolo pyridine-3-one, and
  (7) 2-(N-phenyl carbamoyl)-(5,4b)-isothiazolo pyridine-3-one.

6. The derivative of claim 1 in the form of a salt of an acid selected from the group consisting of hydrochloric acid, hydrobromic acid, acetic acid, citric acid, malic acid, tartaric acid, succinic acid, salicyclic acid and retinoic acid.

7. An anti-acne cosmetic composition for topical application to the skin comprising in an aqueous, alcoholic or hydroalcoholic carrier from 0.1 to 10 weight percent, based on the total weight of said composition, of a N-carbamoyl derivative of (5,4b)-isothiazolo pyridine-3-one having the formula

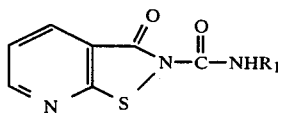

wherein
$R_1$ represents hydrogen, linear or branched alkyl having 1-12 carbon atoms, cycloalkyl having 3-6 carbon atoms, or

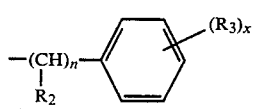

wherein n is 0 or 1, x is 1, 2 or 3, $R_2$ represents hydrogen or lower alkyl having 1-3 carbon atoms and $R_3$ represents hydrogen, lower alkyl having 1-3 carbon atoms, nitro, trifluoromethyl or halogen, the salts thereof with a mineral or organic acid and the optical isomers thereof when $R_2$ represents alkyl and n equals 1.

8. An anti-acne cosmetic composition for topical application to the skin comprising in an aqueous, alcoholic or hydroalcoholic carrier from 0.1 to 10 weight percent, based on the total weight of said composition, of a N-carbamoyl derivative of (5,4b)-isothiazolo pyridine-3-one selected from the group consisting of
  2-(N-methyl carbamoyl)-(5,4b)isothiazolo pyridine-3-one,
  2-(N-butyl carbamoyl)-(5,4b)isothiazolo pyridine-3-one,
  2-(N-isopropyl carbamoyl)-(5,4b)isothiazolo pyridine-3-one,
  2-(N-heptyl carbamoyl)-(5,4b)isothiazolo pyridine-3-one,
  2-(N-nonyl carbamoyl)-(5,4b)isothiazolo pyridine-3-one,
  2-(N-cyclohexyl carbamoyl)-(5,4b)isothiazolo pyridine-3-one,
  2-(N-phenyl carbamoyl)-(5,4b)isothiazolo pyridine-3-one,
  2-(N-phenyl carbamoyl)-(5,4b)isothiazolo pyridine-3-one trans-retinoate,
  2-(N-isopropyl carbamoyl)-(5,4b)isothiazolo pyridine-3-one trans-retinoate,
  2-(N-nonyl carbamoyl)-(5,4b)isothiazolo pyridine-3-one trans-retinoate,
  2-(N-cyclohexyl carbamoyl)-(5,4b)isothiazolo pyridine-3-one trans-retinoate,
  2-(N-nonyl carbamoyl)-(5,4b)isothiazolo pyridine-3-one salicylate, and
  2-(N-cyclohexyl carbamoyl)-(5,4b)isothiazolo pyridine-3-one salicylate.

9. A method for the treatment of acne so as to inhibit the activity of *Corinebacterium acnes* and *Propionibacterium granulosum,* said method comprising applying an amount of an anti-acne cosmetic composition effective to inhibit said *Corinebacterium acnes* and *Propionibacterium granulosum* to the area of the skin affected by acne, said anti-acne composition comprising in an aqueous, alcoholic or hydroalcoholic carrier from 0.1 to 10 weight percent, based on the total weight of said composition, of a N-carbamoyl derivative of (5,4b)-isothiazolo pyridine-3-one having the formula

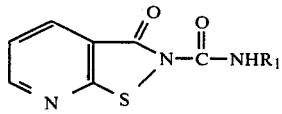

wherein
$R_1$ represents hydrogen, linear or branched alkyl having 1-12 carbon atoms, cycloalkyl having 3-6 carbon atoms or

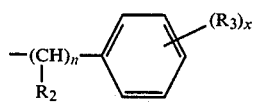

wherein n is 0 or 1, x is 1, 2 or 3, $R_2$ represents hydrogen or lower alkyl having 1-3 carbon atoms, $R_3$ represents hydrogen, lower alkyl having 1-3 carbon atoms, nitro, trifluoromethyl or halogen, the salts thereof with a mineral or organic acid and the optical isomers thereof when $R_2$ represents alkyl and n equals 1.

* * * * *